US008999921B2

(12) United States Patent
Bang et al.

(10) Patent No.: US 8,999,921 B2
(45) Date of Patent: Apr. 7, 2015

(54) PROCESS FOR DIAGNOSING RHEUMATIC DISEASES

(75) Inventors: Holger Bang, Hattersheim (DE); Wigbert Berg, Mainz (DE)

(73) Assignee: Cypress Bioscience, Inc., San Diego, CA (US)

(*) Notice: Subject to any disclaimer, the term of this patent is extended or adjusted under 35 U.S.C. 154(b) by 1207 days.

(21) Appl. No.: 11/597,515

(22) PCT Filed: Jun. 27, 2006

(86) PCT No.: PCT/EP2006/006205
§ 371 (c)(1),
(2), (4) Date: Nov. 27, 2006

(87) PCT Pub. No.: WO2007/000320
PCT Pub. Date: Jan. 4, 2007

(65) Prior Publication Data
US 2009/0155822 A1    Jun. 18, 2009

(30) Foreign Application Priority Data

Jun. 27, 2005    (DE) .................. 10 2005 029 845

(51) Int. Cl.
| A61K 38/02 | (2006.01) |
| C07K 14/47 | (2006.01) |
| G01N 33/564 | (2006.01) |
| A61K 38/00 | (2006.01) |

(52) U.S. Cl.
CPC .............. *C07K 14/47* (2013.01); *G01N 33/564* (2013.01); *A61K 38/00* (2013.01)
USPC ......................................................... 514/2

(58) Field of Classification Search
None
See application file for complete search history.

(56) References Cited

U.S. PATENT DOCUMENTS

2009/0010943 A1*    1/2009    Hill et al. ................... 424/172.1

FOREIGN PATENT DOCUMENTS

| WO | 0047193 A2 | 8/2000 |
| WO | 0074662 A2 | 12/2000 |
| WO | WO 2004/078098 | 9/2004 |
| WO | 2006006205 R | 11/2007 |

OTHER PUBLICATIONS

Hoffman et al (Journal of Cell Science, 1992, p. 687-700).*
Greenspan et al. (Nature Biotechnology 7: 936-937, 1999).*
Bowie et al (Science, 1990, 257:1306-1310).*
Adcocks, C. et al. "Catechins from Green Tea (*Camellia sinensis*) Inhibit Bovine and Human Cartilage Proteoglycan and Type II Collagen Degradation in Vitro." (Journal of Nutrition), Mar. 2002, 341-346, 132:3.
Cerdeno-Tarraga, A.M. et al. "Extensive DNA inversions in the *B. fragilis* genome control variable gene expression." (Science), 2005, 1463-1465, 307:5714.
Haqqi, T.M. et al. "Prevention of Collagen-Induced Arthritis in Mice by a Polyphenolic Fraction from Green Tea." (Proc. Natl. Acad. Sci. U.S.A), Apr. 13, 1999, 4524-4529, 96:8.
Kuwahara, T. et al. "Genomic analysis of *Bacteroides fragilis* reveals extensive Dna inversions regulating cell surface adaptation." (Proc. Natl. Acad. Sci. U.S.A), 2004, 14919-14924, 101:41.
Vimentin [*Homo sapiens*] NCBI accession No. NP_003371 (version 2): First accession date: Apr. 8, 2005; Updated: Feb. 6, 2011 (no change in core peptide sequence).
Carter et al. "Epitope Mapping of a Protein Using the Geysen (PEPSCAN) Procedure." The Protein Protocols Handbook 1996, Part V, 581-593.
Bang et al. "Mutation and citrullination modifies vimentin to a novel autoantigen for rheumatoid arthritis." Arthritis & Rheumatism, 56 (8), 2503-2511, 2007.
DeRooy et al., "Can anti-cyclic citrullinated peptide antibody-negative RA be subdivided into clinical subphenotypes?", Arthritis Research & Therapy 2011, 13:R180, pp. 1-7.
Innala L., et al., Abstract 1—J Rheumatol. Jun. 2008;35(6):1002-8. Epub Apr. 1, 2008, "Antibodies against mutated citrullinated vimentin are a better predictor of disease activity at 24 months in early rheumatoid arthritis than antibodies against cyclic citrullinated peptides".
Szekanecz Z., et al., Abstract 2—Clin Rev Allergy Immunol. Feb. 2008;34(1):26-31. Doi: 10.1007/s12016-007-8022-5. "Anti-citrullinated protein antibodies in rheumatoid arthritis: as good as it gets?".
Nature Medicine vol. 18/No. 6/Jun. 2012—"Autoantibodies target bone".
Ulrike Harre et al., "Induction of osteoclastogenesis and bone loss by human autoantibodies against citrullinated vimentin", The Journal of Clinical Investigation, vol. 122, No. 5, May 2012.
Database EMBL., "Hypothetical Protein BF0713, *Bacteroides fargilis* NCTC9343", Jul. 29, 2004 (XP002424393).
Database EMBL., "Hypothetical Protein BF0786, *Bacteroides fargilis* YCH46", Oct. 1, 2004 (XP002424394).
W. Kraus et al., "Autoimmune Sequence of Streptococcal M Protein Shared with the Intermediate Filament Protein, Vimentin", The Journal of Experimental Medicine, vol. 169 (Feb. 1989) pp. 481-492.
J. Perreau et al., "Nucleotide Sequence of the Human Vimentin Gene and Regulation of its Transcription in Tissues and Cultured Cells", Gene, vol. 62 (1988) pp. 7-16.
R.M. Nelson et al., "A General Method of Site-Specific Mutagenesis Using a Modification of the *Thermus aquaticus* Polymerase Chain Reaction", Analytical Biochemistry, vol. 180 (1989) pp. 147-151.
Hill, J. A. et al., "Cutting Edge: The conversion of arginine to citrulline allows for a high-affinity peptide interaction with the rheumatoid arthritis-associated HLA-DRB1*0401 MHC Class II Molecule," The Journal of Immunology, 2003, vol. 171, pp. 538-541.

(Continued)

*Primary Examiner* — Brian J Gangle
(74) *Attorney, Agent, or Firm* — Millen, White, Zelano & Branigan, P.C.

(57) ABSTRACT

The invention relates to polypeptides reacting with rheumatism-associated autoantibodies. The invention moreover relates to a diagnostic agent comprising any of said polypeptides, to a diagnostic kit comprising said diagnostic agent and to a process for in vitro detection of rheumatic diseases. The invention furthermore relates to a medicament comprising any of said polypeptides and to the use of said polypeptides for preparing a medicament for the prophylaxis and/or treatment of rheumatic diseases.

39 Claims, 8 Drawing Sheets

(56) References Cited

OTHER PUBLICATIONS

Figure 1:
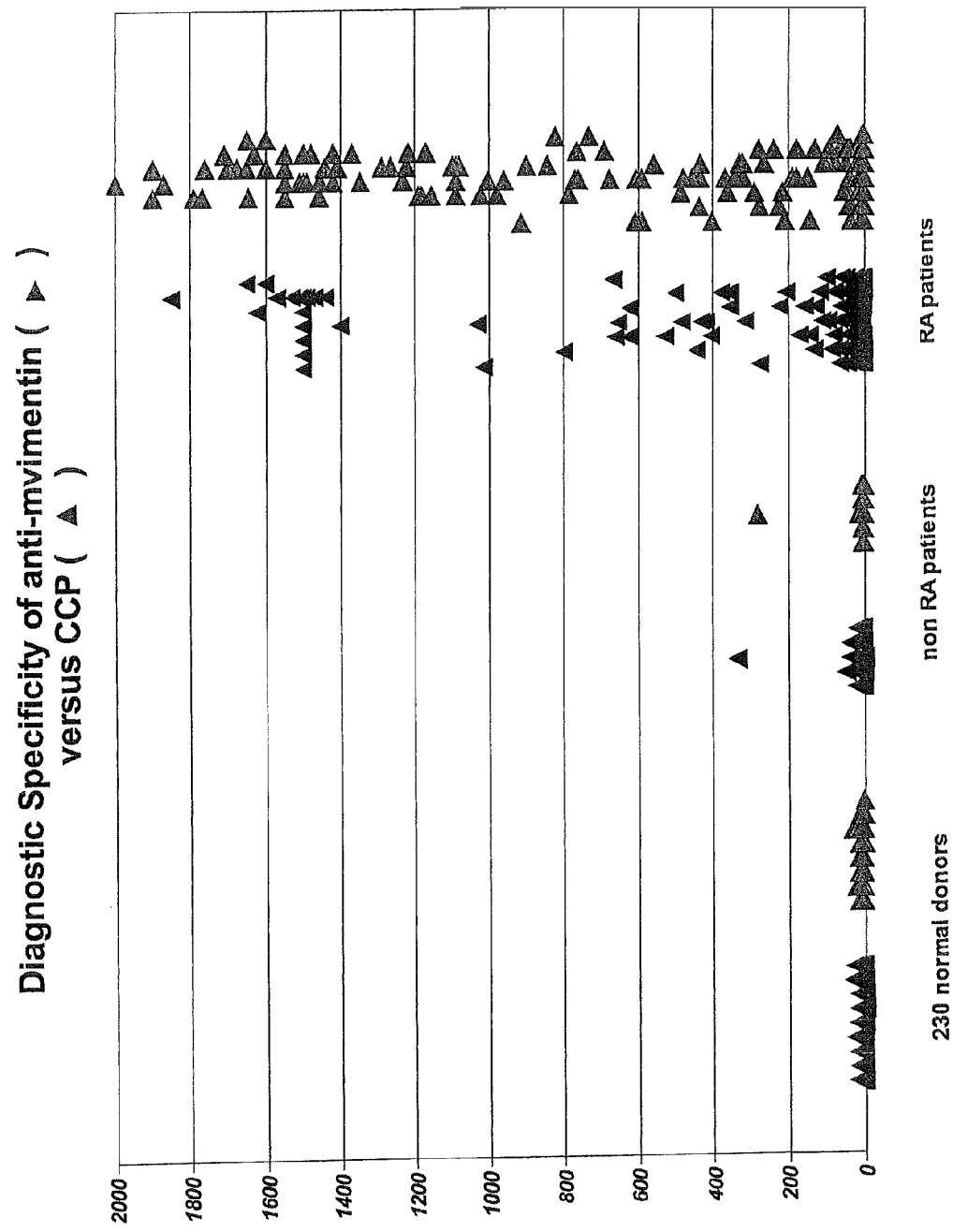

Geysen et al. *PNAS*, 81, 3998-4002, 1984.
Geysen et al., *J. Immunol. Methods*, 259-274, 1987. (Abstract).
Van Der Zee et al. *Eur. J. Immunol.* 1989. 19:43-47.
Maiji et al., *J. of Immunol. Methods*, 134, 23-33. 1990. (Abstract).
Carson et al. *J. Gen. Virol.*, 74, 2669-2677, 1993.
Houghten et al. PNAS, 82, 5131-5135, 1985.
Oftung et al., J Immunol., 141, 2749-54, 1988. (Abstract).
Lee et al., "Microsatellite instability and suppressed DNA repair enzyme expression in rheumatoid arthritis," J Immunol., 1;170(9):4869, 2003.
Harre et al., "Induction of osteoclastogenesis and bone loss by human autoantibodies against citrullinated vimentin," J. Clin. Invest, 122(5):1791-1802.
Kuna et al. "Mutated citrullinated vimentin antibodies in rheumatoid arthritis," Clin Chim Acta, Jan. 18, 2012;413(1-2):66-73.
Partial International Search Report dated Jan. 22, 2007 issued in PCT/EP2006/006205.
Vossenaar E. R. et al., "Anti-CCP antibodies, a highly specific marker for (early) . . . ", Clin. and Applied Immunology Reviews 2004 US, 2004, pp. 239-262.
Database EMBL 4, May 5, 2005, "Vimentin Protein", XP002407716.
Boekel, Van M A M, et al., "Autoantibody Systems in Rheumatoid Arthritis: Specificity . . . ", Arthritis Research, Current Science, London, GB, Nr. 2, 2002, pp. 87-93.
Pinheiro Geraldo Castelar et al., "Anti-cycle citrullinated peptide antibodies in advanced . . . "Annals of Internal Medicine, Aug. 5, 2003, XP002407635, ISSN: 1539-3704.
Schellekens G. A. et al., "Citrulline is an Essential Constituent of Antigenic Determinants recognized by Rheumatoid . . . ", Journal of Clinical Investigation, New York, NY, pp. 273-281, 1998.
Hofmann I, et al., "Interference in vimentin Assembly in-vitro by synthetic peptides derived from the vimentin head domain", Journal of Cell Science, 1992, pp. 687-700.
Vossenaar Erik R., et al., "Rheumatoid arthritis specific anti-Sa antibodies target citrullinated vimentin", Arthritis Research, Current Science, London, Feb. 5, 2004, pp. R142-R140.
Office Action for related European Patent Application No. 06 762 214.2, dated Jan. 9, 2015 with partial English translation listed on Information Disclosure Statement Transmittal.
UniProt Accession P48670 Excerpt dated Feb. 1, 1996.

\* cited by examiner

PROCESS FOR DIAGNOSING RHEUMATIC DISEASES

The invention relates to polypeptides reacting with rheumatism-associated autoantibodies. The invention moreover relates to a diagnostic agent comprising any of said polypeptides, to a diagnostic kit comprising said diagnostic agent and to a process for in vitro detection of rheumatic diseases. The invention furthermore relates to a medicament comprising any of said polypeptides and to the use of said polypeptides for preparing a medicament for the prophylaxis and/or treatment of rheumatic diseases.

Rheumatic diseases, in particular pain around the joints and of the musculoskeletal system, are among the most common diseases in Germany. A laboratory assay which enables said pain to be attributed to harmless muscle tenseness, arthrosis or to the most frequent and severe of said diseases, rheumatoid arthritis (RA) is not known to date.

Rheumatoid arthritis is an autoimmune disease in which the defense mechanisms of the human body erroneously regard endogenous joint cartilage as foreign and hostile and attack said cartilage. Approximately 1 out of 100 humans in western European countries suffers from rheumatoid arthritis. The disease progresses very rapidly in the first few months.

An important key strategy in modern rheumatology is therefore the early use of biological drugs which modify the course of the disease. Numerous clinical studies have shown that very good therapeutic success and response rates can be achieved using suitable active compounds, for example TNF antagonists, if said compounds are used in patients already in the early stage. Rheumatologists try to utilize the narrow time window between the onset of the disease and the occurrence of structural joint damage. To date, however, no reliable and sensitive detection of rheumatoid arthritis within said time window has been disclosed in the prior art.

Rheumatoid arthritis is diagnosed according to the classification criteria of the ACR (American College of Rheumatology). According to the criteria of the ACR, the rheumatoid factor is currently the fundamental serological indicator for diagnosing rheumatoid arthritis (RA). Rheumatoid factors are a subgroup of immunoglobulins which are distinguished by immunological cross reaction to the Fc region of immunoglobulin G (IgG).

However, the presence of a rheumatoid factor is not limited to disorders of the rheumatic type (differential-diagnostic evidence), and rheumatoid factors are also found in the serum of patients suffering from infectious diseases, hyperglobulinemias, lymphoproliferative B cell disorders, and generally in the older population.

Usually, elevated concentrations of rheumatoid factors are associated with a more severe cause of the disease. Said concentrations do not correlate with the degree of activity and the therapeutic success. A sensitive and specific prognosis of the onset of rheumatoid arthritis cannot be made on the basis of the concentration of rheumatoid factors. Healthy persons have an elevated rheumatoid factor concentration without falling ill, whereas patients without rheumatoid factors suffer from a very aggressive form of rheumatoid arthritis.

Other serological markers such as anti-citrulline antibody (CCP) or the initial HAQ score which is used to assess abilities in daily life or X-ray or computer tomography (CT) imaging provide only little information on the early form and are, by themselves, not meaningful enough in order to be able to assess the prognosis of the patient.

In order to optimize the existing classification criteria of the ACR, the American College of Rheumatology proposes seven classification criteria which indicate a poor prognosis:
1 morning stiffness of the joints lasting more than one hour,
2 arthritis of three or more joints,
3 inflammation of at least three joint areas at the same time,
4 hand joints or finger joints are likewise affected,
5 bilateral tenderness of metacarpophalangeal joints to pressure,
6 erosions on radiographs,
7 detection of special rheumatoid factors and anti-perinuclear factor positivity (APF).

Autoantibodies to the "anti-perinuclear factor" were first described by Young et al. for patients having rheumatoid arthritis (Young, B. J. J. et al., Antikeratin antibodies in rheumatoid arthritis, B.M.J., 2 (1979), 97-99). Owing to their specific reaction to the keratinous epithelium of the stratum corneum on rat esophagus sections, keratin has been considered for a long time to be the corresponding antigen (Vincent, C. H. et al.; High diagnostic value in rheumatoid arthritis of antibodies to the stratum corneum of rat oesophagus epithelium, so-called "antikeratin antibodies", Ann. Rheumat. Dis. 48 (1989), 712-722). For this reason, the antibodies are even today referred to as antikeratin antibodies (AKAs) (Vincent, C. H. et al, Natural IgG to Epidermal Cytokeratins vs IgG to the Stratum Corneum of the Rat Oesophagus Epithelium, so-called "Antikeratin Antibodies", in Rheumatoid Arthritis and other Rheumatic Diseases; J. of Autoimmunity 4 (1991), 493-505; Paimela, L. et al., Antikeratin antibodies: diagnostic and prognostic markers for early rheumatoid Arthritis, Ann. Rheumat. Dis., 51 (1992) 743-746).

In addition, later studies have demonstrated that AKAs or APFs are also recognized by anti-filaggrin antibodies. Thus the basic protein filaggrin has been identified as a target antigen. The 40 kDa protein aggregates cytokeratin filaments and assists in forming the intracellular fiber matrix of the keratinous cells (Simon, M. et al., The Cytokeratin Filament-Aggregating Protein Filaggrin is the Target of the So-called "Antikeratin Antibodies", Autoantibodies Specific for Rheumatoid Arthritis, J. Clin. Invest., 92 (1993), 1387-93).

Since sera containing APFs, AKAs and anti-filaggrin antibodies react in the same way, these antibody systems appear to be identical. Anti-filaggrin antibodies of the IgG type which have a specificity of more than 99% are a highly specific marker for rheumatoid arthritis. Said antibodies can in principle be detected early and precede the clinical symptoms. Several studies found positive correlations with respect to severity and activity of the disease. Anti-filaggrin antibodies do not correlate with age, sex or duration of the disease. They can be detected in approx. 34% of rheumatoid factor-negative patients and are a variable diagnostic aid here.

Using currently customary methods, however, said antibodies can be found in the serum only in approx. 40% of cases.

It was therefore the object of the present invention to provide novel polypeptides for detecting antibodies associated with rheumatic diseases, in particular antibodies associated with rheumatoid arthritis, which polypeptides make possible a sensitive and specific diagnosis, classification and prognosis of rheumatic diseases, in particular of pain around the joints and of the musculoskeletal system.

When analyzing the binding of antibodies to native vimentin, i.e. APF positivity or anti-Sa reactivity (E. R. Vossenaar et al; Rheumatoid arthritis specific anti-Sa antibodies target citrullinated vimentin; Arthritis Res. Ther. 6(2), (2004), 142-150)), we have now found that native vimentin which has been disclosed in the prior art as being nonreactive immunologically (C. A. Hitchon et al.; Immune features of seronegative and seropositive arthritis in early synovitis studies; Curr. Opin. Rheumatol. 14(4), (2002), 348-353) is present in the form of mutated immunologically reactive variants. This finding is unexpected, since the prior art previously assumed that vimentin must be citrullinated in order to be immunological reactive. We were able to prove this assumption wrong by enriching immunologically reactive vimentin variants with mutated sequences from human monocytes by means of differential immunoaffinity chromatography. These mutated variants of native vimentin differ from native vimentin in the presence of additional arginine residues and, where appropriate, further sequence differences. They react to human RA-associated antibodies and surprisingly have higher specificity and sensitivity than the citrullinated peptides disclosed in the prior art.

The invention therefore relates to a polypeptide derived from native vimentin having SEQ ID No. 1, which differs from the native sequence by the presence of at least one additional arginine residue.

Said additional arginine residues are preferably inserted in the sequence by way of substitution of other amino acid residues of native human vimentin. The polypeptide preferably has an arginine residue in at least one of positions 16, 17, 19, 41, 58, 59, 60, 68, 76, 140, 142, 147, 363, 406 or 452. Particularly preferred positions are 41, 58, 59, 60 and/or 68. For example, the polypeptide has an additional arginine residue in at least one, two, three or four positions.

In another embodiment, the polypeptide moreover has, compared to the native sequence, an additional leucine residue in at least one of positions 3, 20, 33, 36, 37, 94, 165, 361, 399 or 426, preferably in positions 33, 36 and/or 37. For example, the polypeptide has an additional leucine residue in at least one, two, three or four positions.

In another embodiment, the polypeptide has, compared to the native sequence, an additional proline residue in at least one position, for example in any of positions 21, 41, 43, 50, 54, 62, 64 or 89, preferably in positions 41, 43, 50, 54, 62, and/or 64. For example, the polypeptide has a proline residue in at least one, two, three or four positions.

In another embodiment, the polypeptide has, compared to the native sequence, an additional threonine residue in at least one position, for example in any of positions 24, 35 or 99. For example, the polypeptide has a threonine residue in at least one, two or three positions.

In a further embodiment, the polypeptide has, compared to the native sequence, an additional tyrosine residue in at least one position, for example in any of positions 25, 39, 42, 49, 55 or 67. For example, the polypeptide has a tyrosine residue in at least one, two, three or four positions.

In another embodiment, the polypeptide contains at least one arginine residue in the form of a citrulline residue, for example in at least one of positions 4, 12, 23, 28, 36, 45, 50, 64, 71, 100, 320, 364 or 378. For example, the polypeptide has a citrulline residue in at least one, two, three or four of said positions. Alternatively, however, said polypeptide may also be a citrulline-free polypeptide.

Preferred example of muteins of human vimentin have a sequence having SEQ ID No. 2, 3, 4, 5, 6, 7, 8 or 9.

The invention further relates to a fragment of any of the abovementioned polypeptides, which has been derived from native vimentin having SEQ ID No. 1 and which comprises at least one region containing at least one arginine residue and which exhibits reactivity to autoantibodies associated with rheumatoid diseases. Said fragment is preferably located within the region of positions 10-145. Particular preference is given to said fragment being located within the region of positions 30-70. A preferred example of a fragment is the fragment 51-65 (C2). The fragment is preferably at least 6, particularly preferably at least 8, amino acids and up to 120, preferably up to 100, and particularly preferably up to 50, amino acids in length.

The invention further relates to peptide derivatives of the abovementioned polypeptides or fragments. For example, the peptide derivative may be a retro/inverso polypeptide, i.e. an inverse polypeptide of the above-described polypeptides which is prepared from D-amino acids according to a mirror image of said polypeptides, a retro polypeptide which has a "reverse" sequence and a retro-inverso polypeptide which is a mirror image of the above-described polypeptides and also has a "reverse" sequence.

Further examples of peptide derivatives are side-group-, amino terminus- or/and carboxy terminus-modified polypeptides of an amino group, for example polypeptides which have been modified, for example, with a carboxylic acid or an alkyl radical or which have been modified on a carboxylic acid group with an amino group or an ester group. Said polypeptides and/or peptide derivatives may also be cyclic peptides.

The invention further relates to a nucleic acid coding for an above-described polypeptide. Examples of suitable nucleic acids are DNA and RNA, in particular cDNA. Said nucleic acids may be cloned for recombinant preparation of said polypeptides into customary eukaryotic or prokaryotic vectors and expressed in suitable host cells.

The invention further relates to a diagnostic agent comprising one or more of the above-described polypeptides or fragments thereof. Said diagnostic agent may comprise said polypeptide or said fragment in a free or in a carrier-bound form.

The fact that the polypeptides of the invention prove to be highly specific and highly sensitive antigens for diagnosing antibodies in body fluids of patients having rheumatic diseases, in particular having inflammatory diseases of the joints and of the musculoskeletal system, particularly preferably of rheumatoid arthritis, can be described as a particular surprise. Preferred body fluids in accordance with the invention are blood, serum or plasma, with particular preference being given to serum.

The diagnostic agent of the invention has a number of advantages. Thus it is possible to bind both monomeric and multimeric antibodies efficiently, since the polypeptides contain a plurality of antibody binding sites. Another advantage of the mutated polypeptide is its enabling a diagnostic agent to be provided which can be used to identify patients having inflammatory and chronic diseases of the joints and of the musculoskeletal system, in particular those having rheumatoid arthritis, with a specificity of 99% and a sensitivity of 85%.

The prior art has up to now not disclosed any comparably specific or sensitive diagnostic agent enabling rheumatic diseases, in particular rheumatoid arthritis, to be detected using a citrulline-free protein or peptide (P. J. Utz, Death, autoantigen modifications, and tolerance; Arthritis Res., 2, (2000), 101-114).

The invention further relates to a diagnostic kit for use in detecting rheumatic diseases, in particular rheumatoid arthritis, which kit comprises an above-described diagnostic agent. In addition, the diagnostic kit may comprise customary components such as buffers, solvents and/or labeling groups.

Suitable carriers are macromolecules such as DNA, RNA, medically compatible polymers such as, for example, polyethylene, poly-D,L-lactides, poly-D,L-lactide coglycolides, synthetic biopolymers such as, for example, polylysines and dextrans, and proteins such as, for example, serum albumin and hemocyanine. Preference is given to using dextrans in a "hydrocoating coating process" (Gregorius, K., Mouritsen, S. and Elsner, H. I., Hydrocoating: a new method for coupling biomolecules to solid phases, J. Immunol. Methods 12 (1995), 65-73).

The invention further relates to a process for in vitro detection of rheumatic diseases, in particular of rheumatoid arthritis, which process comprises determining the concentration of autoantibodies in a body fluid. Said process permits a diagnosis to be made and classification and/or evaluation of the severity of the disease. The detection reagent used is the above-described diagnostic agent or the above-described diagnostic kit.

Detection methods which may be used in the process of the invention are any methods customary in the field of diagnostics, such as
(a) enzymological methods,
(b) methods based on luminescence, or
(c) radiochemical methods.

Preferred suitable detection methods in the process of the invention are a radioimmunoassay, a chemoluminescence immunoassay, an immunoblot assay or an enzyme immunoassay, for example an ELISA.

One embodiment of the process of the invention comprises adding the body fluid to be analyzed as sample to an above-described polypeptide bound to a carrier. After incubation of said sample, unbound components are washed away. The autoantibodies to be detected which specifically bind to said polypeptide are detected by means of a secondary antibody carrying a labeling group.

Examples of suitable secondary antibodies in the process of the invention are antibodies directed to human antibodies such as, for example, IgG, IgM, IgA or/and IgE, for example the Fc portion of human IgG.

Examples of suitable labeling groups in the process of the invention are an enzyme such as, for example, peroxidase or alkaline phosphatase, a radiolabel or a luminescent labeling group such as, for example, acridinium compounds.

Alternatively, it is also possible to carry out a competitive inhibition assay using the polypeptides of the invention, which assay comprises inhibiting the binding of a labeled rheumatoid arthritis (RA) autoantibody in the presence of a sample, if said sample likewise contains RA autoantibodies.

The peptides of the invention may also be used as means for prognosis or/and progression control in the treatment of rheumatic diseases, in particular rheumatoid arthritis. Prognostic means which are preferred here are peptides from the region of positions 30-65 or/and positions 55-70.

Another object of the present invention was to provide medicaments which selectively inhibit or prevent the formation of autoimmune complexes in connection with rheumatic diseases, in particular inflammatory processes, particularly preferably in the inflamed joint, but which do not cause general blocking of antibody production.

This object is achieved according to the invention by a medicament which comprises an above-described polypeptide or fragment and is suitable for applications in human or veterinary medicine. Said medicament may be used, for example, for extracorporeal treatment of body fluids, for example blood or plasma, in order to capture autoantibodies comprised therein using solid phase-bound antibodies and to reintroduce the treated body fluid into the patient.

The examples according to the invention surprisingly reveal that the polypeptide of the invention is an antigen primarily related to the course of the disease or is even the protein primarily initiating said disease. The course of the disease may be influenced in a beneficial manner by selectively removing antibodies from the body fluids of patients.

It is furthermore possible to administer the polypeptides or fragments thereof also directly in the form of a pharmaceutical composition which may comprise pharmaceutically compatible carriers, solvents and/or excipients.

Said pharmaceutical composition may be administered in the form of a tablet, a capsule, a solution, a suspension, an aerosol, a spray (nasal or throat spray), a gel, a patch, etc.

The medicament may be administered by any known methods, particular preference being given to oral and intravenous administrations.

The dose may vary depending on the type and severity of the disease and is usually in the range from 1 to 2000 mg/day, preferably in the range from 10 to 200 mg/day.

RA patients may furthermore undergo therapy by means of the identified short, synthetic protein epitopes of the above-described polypeptides (inter alia C2 epitope), which derive from the amino acid sequence of native vimentin.

The analysis of B-cell epitopes of RA patients yielded the surprising finding that 91% of all patients interact with a short synthetic, linear peptide epitope (C2 epitope) of the polypeptide of the invention.

Furthermore, it was found by way of experiments on mice that the latter, after such a treatment, produced immune cells which successfully suppress division of antigen-specific immune cells.

Controlling the course and the success of the therapy of rheumatic diseases, in particular rheumatoid arthritis, is possible according to the current diagnostic methods only by means of the complicated and time-consuming method of Disease Activity Score (DAS). This method involves calculating the number of swollen joints, the number of painful joints, the inflammation parameters (BSR or CRP) and recording the state of the patient on a visual analog scale.

Said four individual components are summed up according to a formula. The resulting score provides relatively reliable and objective information on the actual activity of the disease and the quality of therapy for the patient.

The polypeptides of the invention now enable the course and the success of the therapy of rheumatic diseases, in particular rheumatoid arthritis, to be controlled.

For example, a rapid and effective therapy was observed in patients who cross-reacted with the polypeptide in positions 30 to 65, with said therapy partially coming to a positive conclusion in the form of a complete recovery after two years.

Patients having low disease activity (average DAS score of 2.8) were identified by an ELISA based on the polypeptide of the invention (<300 U/ml on average). Correlating with the success of treatment (DAS score less than 1.5 after treatment) with sulfasalazine or cortisone, the antibody titers were reduced to, on average, ⅙ of the starting value in the course of 1-2 years.

Patients suffering from severe rheumatoid arthritis (average DAS score of 4.9) had, on average, an antibody titer of >1000 U/ml. With no significant alteration in the DAS score due to treatment with Remicade and/or methotrexate, the amount of antibodies to the polypeptides of the invention was reduced by approx. 30-50% in 50% of patients. In parallel with the altered antibody titer, patients reported during anamnesis a substantially more positive overall evaluation of their subjective situation regarding the disease, i.e. the diagnostic agent of the invention is also suitable for quality control of the therapy of a severe rheumatoid arthritis.

A substantial advantage is the fact that for the first time it is possible to give qualitatively and quantitatively reliable information on the type, the course and therapy of rheumatoid arthritis within a few minutes.

This surprising finding led to the realization that the polypeptides of the invention may be used therapeutically because, surprisingly, their use can be expected to reduce the previous undesired effects of medicaments, with the efficacy of the latter being retained.

More specifically, the polypeptides of the invention surprisingly enabled a novel, previously unknown principle of action for the treatment of rheumatic diseases, in particular inflammations, to be provided. The spectrum of action of the polypeptides of the invention is different from that of previously known inhibitors of inflammations, since selectively only antibody-dependent mediators can be produced in reduced numbers. Another advantage of the polypeptide of the invention is the fact that the spectrum of side effects is probably considerably smaller than that of medicaments known from the prior art, since no cross reaction with antibodies of healthy blood donors has been observed.

The above-described diagnostic and therapeutic agent of the invention may therefore be applied to the diagnosis, prophylaxis or treatment of any symptoms based on vimentin-dependent processes.

The present invention further relates to the hypothetic proteins, BF0786 and BF0713, of the paradontitis pathogens *Bacteroides forsythus* and *Prevotella intermedia*, which have been found to be initiators of rheumatic diseases, in particular of a chronic inflammatory disease of the joints and of the musculoskeletal system.

Said proteins and fragments thereof are therefore suitable for preparing a diagnostic agent, a diagnostic kit or a medicaments for detection, prophylaxis and/or treatment of rheumatic diseases, in particular of pain in joints and of the musculoskeletal system. With regard to diagnostic and pharmaceutical applications, reference is made to the comments above on the vimentin analogs.

The BF0786 protein and its sequence have been described by Kuwahara, T. et al. (Kuwahara, T. et. al., Proc. Natl. Acad. Sci. U.S.A 101 (41), 14919-14924 (2004)). The BF0713 protein and its sequence have been described by Cerdeno-Tarraga, A. M. et al. (Cerdeno-Tarraga, A. M. et. al., Science 307 (5714), 1463-1465 (2005)). Medical applications in the field of diagnostics and therapy have not been disclosed previously.

Another object of the present invention was to find substances which selectively block the formation of autoimmune complexes of rheumatism-associated autoantibodies with autoantigens, in particular with vimentin, i.e. which prevent only the response of antibodies involved in pathogenesis but which do not generally influence antibody production and response and which therefore enable a sensitive and specific therapy or prophylaxis of rheumatism-associated diseases, of pain around the joints and of the musculoskeletal system.

This object has now been found to be solved by the ingredients of green tea. Tariq, M. et al., "Prevention of collagen-induced arthritis in mice by a polyphenolic fraction from green tea", Proc. Natl. Acad. Sci. USA, Vol. 96, pages 4524-4529, (1999) disclose epigallocatechin gallate (EGCG), an ingredient of green tea. Said ingredient binds to vimentin and blocks phosphorylations (S. Ermakova et al., The intermediate filament protein vimentin is a new target for epigallocatechin gallate; J. Biol. Chem. 280 (17), (2005), 16882-16890). Using epigallocatechin gallate it was possible to show that the formation of autoimmune complexes of autoantibodies to mutated vimentin can be blocked in a concentration-dependent manner.

Competition experiments demonstrated that the non-binding substance, epicatechin (EC), blocks antibody binding only up to a maximum of 10%. A concentration of 10-100 μg/ml epigallocatechin gallate (EGCG) was shown to block no more than 45% of antibody binding.

If, however, green tea is extracted with a suitable organic or organic-aqueous solvent or solvent mixture, for example a mixture of dimethyl sulfoxide (DMSO), ethanol and water, it is surprisingly possible to achieve almost complete blocking of autoimmune complex formation by using small amounts of said extract. Furthermore, it is also possible to use products which are obtainable from such extracts, for example by drying, lyophilization, fractionation etc. The effect of said extract runs counter to the prior art, since a specific blocking of antibody reactions has previously been disclosed neither for the known individual substances of green tea nor for a natural substance mixture. The extract of the invention was unable to alter significantly the formation of antibody complexes in sera of patients having other autoimmune diseases.

These results can be regarded as being extremely surprising, since no independent binding to a mutated vimentin has been disclosed in the prior art previously. Furthermore, the interaction of the ingredients of green tea with antibodies has not been disclosed in the prior art.

Moreover, it has previously been disclosed only that EGCG a) has antioxidative action, b) captures reactive intermediates of carcinogenic substances, c) inhibits carcinogen-activating enzymes and d) inhibits nitrosation and cell proliferation (in particular of tumor cells).

Finally, the invention further relates to the use of an above-described peptide, an above-described peptide fragment, an above-described retro-inverso polypeptide or a cyclic peptide for finding blocking natural substances and/or chemical substances for antibody-driven inflammatory reactions.

In addition it is possible to develop, on the basis of the peptide of the invention, bioassays which can be used to analyze natural substance libraries, combinatorial libraries and chemical libraries for the presence of anti-inflammatory substances. Using disease-associated antibodies it is possible to identify and purify substances from the above mixtures, which directly or indirectly block the antigen of the invention by way of blocking said antibody. In an animal experiment, these substances were shown to result in a rheumatoid arthritis-delaying and, at higher doses, complete recovery.

The present invention is furthermore to be illustrated by the following figures and examples.

FIGURE LEGENDS

FIG. 1: Comparison of the diagnostic specificity of detecting RA autoantibodies by using mutated vimentin (•) compared to citrullinated peptides (CCP) (▲).

Figure 2:
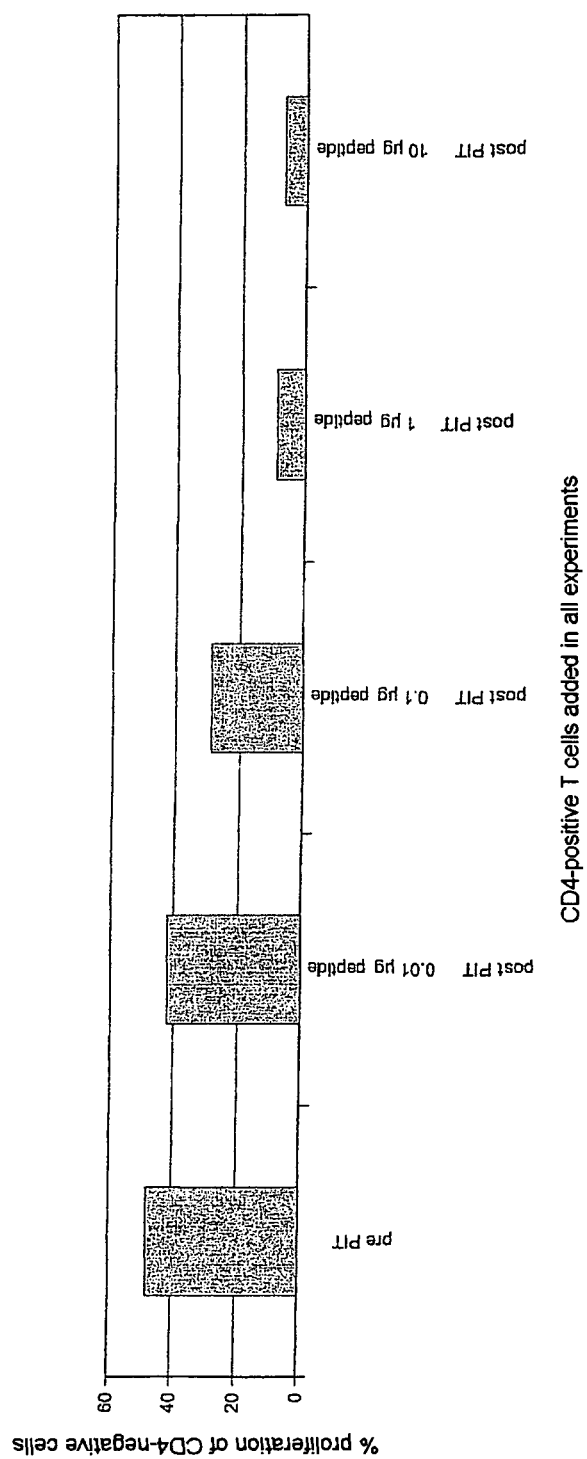

FIG. 2: Isolated CD4-positive T cells suppress the proliferative response of CD4-negative cells after a peptide immunotherapy.

Figure 3:
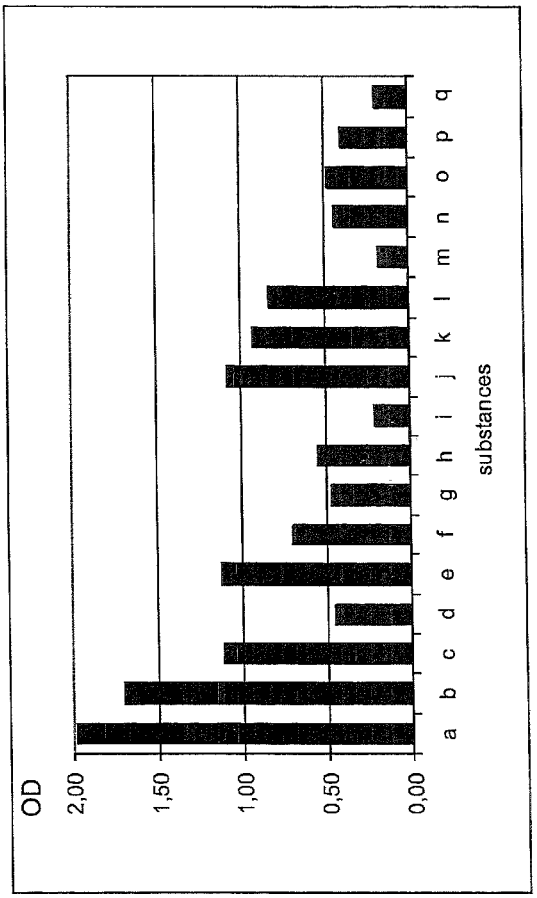

FIG. 3: Inhibition of the response of antibodies from RA sera by extracts from green tea, mutated vimentin and combinations thereof.

Figure 4:
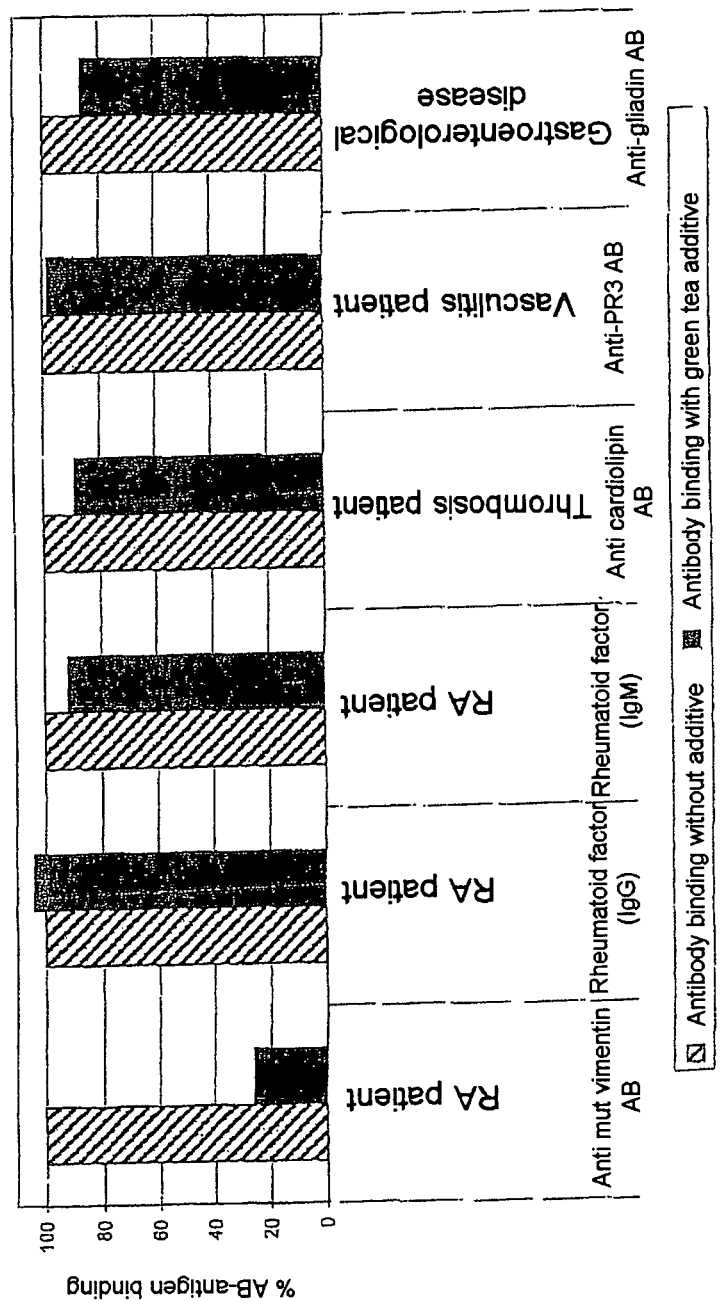

FIG. 4: Selectivity of extracts from green tea in the blocking of autoantibodies from RA patients.

Figure 5:
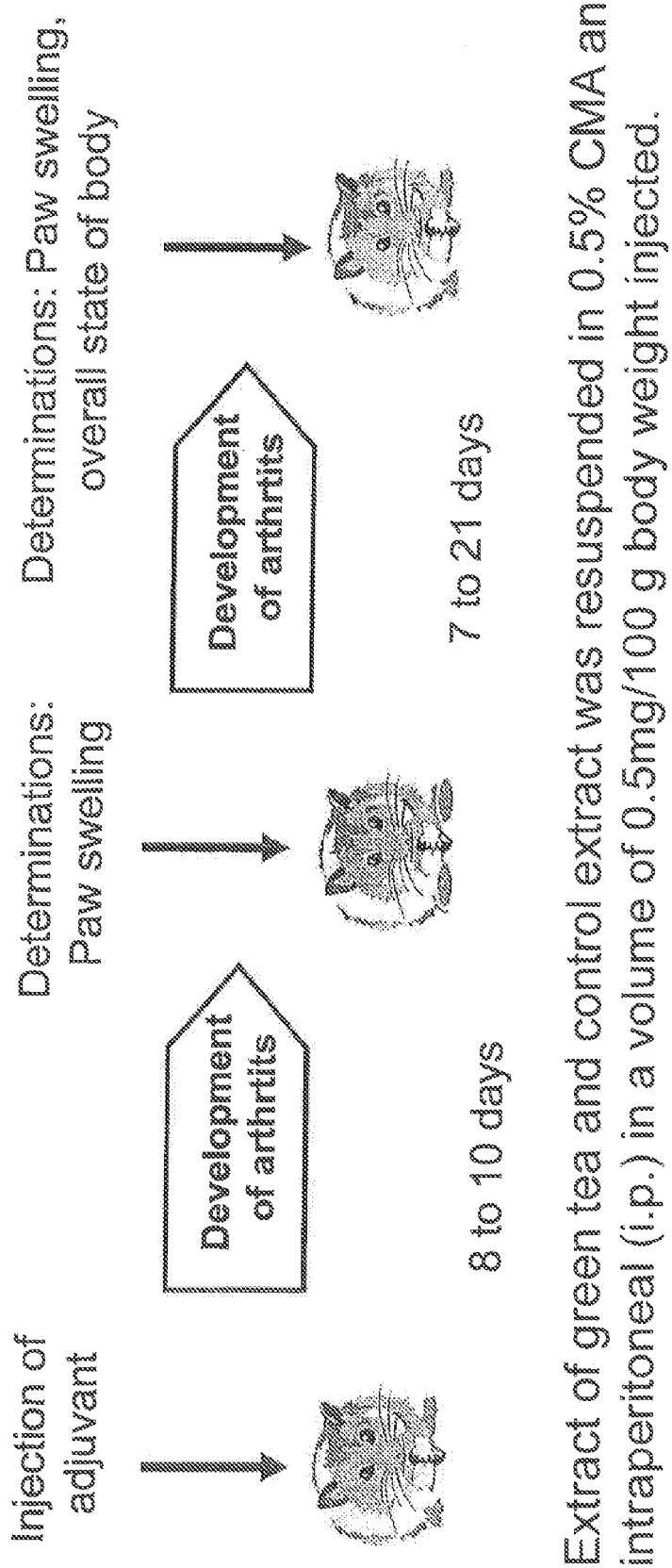

FIG. 5: General representation of an athritis antimal model
FIG. 6-8: Efficacy of extracts from green tea in vivo

EXAMPLES

Example 1

Identification of Mutated Variants of Human Vimentin as RA-Associated Antigens

A cell extract was prepared from U937 cells (human monocyte cell line). Citrullinated proteins were removed from said cell extract by preabsorption using a commercial anti-citrulline antibody. Subsequent affinity chromatography using chicken anti-vimentin antibodies provided an eluate from which vimentin variants were isolated which crossreacted with antibodies of patients having RA. The vimentin variants obtained were further characterized by reverse phase chromatography, proteolytic digest and amino acid sequencing. As a result thereof, the polypeptides described below and having the amino acid sequences SEQ ID No. 2-9 were identified.

Example 2

Detection of RA-Associated Autoantibodies, Using a Mutated Vimentin as Detection Antigen A recombinant, mutated variant of native vimentin of Example 1 (SEQ 9) was expressed in E. coli and purified by means of affinity chromatography using the His-tag. A 2 mg/ml solution of the purified protein was pretreated with unfolding buffer (50 mM Tris, 2 M guanidine hydrochloride, 5 mM CaCl$_2$, 2 mM DTT, 0.5 mM EDTA, 5 mM methylammonium chloride, pH 7.4), and for at least 14 hours at 4° C., and subsequently diluted 1:1000 in PBS. 100 µl of this solution were introduced to the cavities of a microtiter plate (manufacturer: COSTAR) at 4° C. overnight. Unbound polypeptide was removed by washing three times (175 µl, buffer PBS/0.05% TWEEN). Potentially unspecific crossreactions were blocked by incubating the cavities with 150 µl of a 3% bovine serum albumin (BSA) solution in PBS. The blocked, emptied plate was dried at 37° C. for 30 min and stored at 4' under desiccating conditions.

Microtiter plates prepared in this way were employed in quantitative detection of autoantibodies to mutated vimentin according to the principle of the indirect enzyme immunoassay. Detection of autoantibodies to CCP (citrullinated peptide) was carried out for comparison. For this purpose, samples of sera of healthy volunteers and/or patients having different diseases were diluted 1:100 with 1% BSA/PBS and incubated in the cavities for 30 minutes. Unbound serum antibodies are removed by repeatedly washing with PBS/ 0.05% TWEEN. Subsequently, enzyme-labeled detection antibodies (in particular peroxidase-conjugated anti-human IgG antibodies, 1:10 000 dilution) were incubated for 15 minutes.

After washing off the excess detection antibody, 100 µl of a substrate solution (TMB (3,3',5,5'-tetramethylbenzidine) tablet, dissolved in 10 ml of 0.05 M phosphate-citrate buffer, with 8 ml of hydrogen peroxide being added shortly before use) were added for 15 minutes. Addition of 100 µl of 1 M HCl stopped the reaction, with the reaction product turning yellow. The intensity of the yellow stain was determined photometrically at 450 nm, with absorption being directly proportional to the autoantibody concentration searched for.

The following results were obtained here:

| Serum number | Diagnosis | Mutated vimentin OD at 450 nm | CCP [U/ml] |
|---|---|---|---|
| 1 | Normal serum | 0.127 | |
| 2 | Blood donor | 0.089 | 6.5 |
| 3 | Hepatitis | 0.107 | 12.5 |
| 4 | *Borrelia arthritis* | 0.167 | 17.7 |
| 5 | Rheumatoid arthritis | 0.784 | 4.6 |
| 6 | Rheumatoid arthritis | 0.984 | 361.4 |
| 7 | Rheumatoid arthritis | 2.456 | 1156.5 |
| 8 | Rheumatoid arthritis | 1.709 | 8.6 |
| 9 | Rheumatoid arthritis | 1.342 | 1453.1 |

All patient sera for which "rheumatoid arthritis" had been diagnosed showed, when measured in a Tecan "SPECTRA" photometer, distinctly elevated absorption values compared to the normal sera and sera of patients suffering from other diseases.

Example 3

Development of a Diagnostic Agent Based on Mutated Variants of Native Vimentin

To develop a diagnostic agent based on a mutated vimentin, different mutated polypeptide variants of native vimentin (see Example 1) were cloned and expressed in E. coli. Sera of a collective of patients (approx. 100) having rheumatoid arthritis (RA), as defined by the ACR criteria, were used in order to identify the polypeptide variant having the highest sensitivity in detecting autoantibodies in RA. For this purpose, the expressed and purified proteins were introduced as a coating to microtiter plates, analogously to Example 2, and the crossreaction of said autoantibodies in RA patients was analyzed in a classical ELISA assay.

The mutated sequences obtained in a first screening process were combined in further reaction mixtures in order to obtain the highest possible sensitivity. The specificity of the mutated polypeptide variant found as a diagnostic agent for RA was investigated by using sera of 34 patients having different autoimmune diseases (inter alia SLE, Sjögren syndrome, IDDM) and sera of 53 healthy humans. The mutated polypeptide variants finally obtained were introduced as coating to microtiter plates analogously to Example 2.

Using the mutated variant of Example 2, it was surprisingly possible to achieve higher specificity (>98%) and sensitivity in the analysis of the autoantibodies of RA patients and of patients having other autoimmune diseases than that disclosed in the prior art for citrullinated peptides (CCP) (FIG. 1).

Example 4

Determination of Autoepitopes in Mutated Vimentin

Anti-vimentin antibodies were assayed in an ELISA with regard to their binding capacity to overlapping biotinylated, synthetic 17mer peptides of mutated vimentin (see Example 2). The main question here was, whether the antibodies of the patients having RA are directed to the same B-cell epitopes.

Surprisingly, 91% of the sera in the cohort of 102 patients having RA and different anti-vimentin antibody titers reacted with the linear peptide sequence from the amino terminal region of vimentin. Crossreactions to the carboxy terminal region or the α-helical, rod-like domain in the center were not observed. Sera of healthy volunteers and patients having other autoimmune diseases (inter alia Sjögren syndrome, systemic lupus erythematosus or vasculitis) showed no response to the vimentin peptide sequences.

A particularly high reactivity was found in the region of amino acids 30-70, in particular in the region of amino acids 50-65.

Example 5

Making a Prognosis for RA Patients

RA progresses in a very different manner, and decisions on the therapeutic approach are not final but need to be continuously controlled and adapted when necessary. Therefore, 21 patients undergoing a drug therapy of RA were analyzed with respect to the response to the polypeptides of the invention. In a follow-up analysis (at least 7 takings per patient over 1-2 years), the crossreaction to overlapping, biotinylated, synthetic peptides of mutated vimentin (see Example 4) was characterized in an ELISA. It was found that, for example in RA patients crossreacting with a peptide in positions 30-65 of the vimentin sequence, a rapid and effective therapy is observed which partially resulted in a positive conclusion with complete recovery after 2 years. In contrast it was not possible to register a therapeutic success from the patients' documents in any of the cases investigated of RA patients crossreacting with a peptide in positions 55-70. Healthy patients exhibited no crossreaction to any of the analyzed peptides.

On the basis of these data, the polypeptides of the invention may be used as a diagnostic agent in order to control the course and the success of the therapy of rheumatoid diseases, in particular rheumatoid arthritis. That is to say, a quantitative ELISA using the peptides of the invention can divide patients into drug "responders" and "non-responders" even at the beginning of said therapy.

Example 6

Therapeutic Efficacy of Peptides

Particular messengers are responsible for the inflammatory processes in the mucosa of the joints, in cartilage and in bone. The best-known representative is tumor necrosis factor (TNF). For years, there has been a transgenic mouse model for chronic polyarthritis, which from the outset has substantially assisted the anti-TNF therapy. These mice overexpress human TNF sufficiently in order to develop a severe, chronic, destroying polyarthritis.

Against this background, said transgenic mice were treated either only with a physiological saline solution or were injected with a solution of 1 µg of a peptide (50-65) of mutated vimentin (in analogy to Puga Yung et al., Epitope-specific immunotherapy induces immune deviation of proinflammatory T cells in rheumatoid arthritis, PNAS 2004 101: 4228-4233 and Zwerina et al., Single and combined inhibition of tumor necrosis factor, interleukin-1, and RANKL pathways in tumor necrosis factor-induced arthritis: effects on synovial inflammation, bone erosion, and cartilage destruction. Arthritis Rheum. 2004 Jan; 50(1):277-90). Subsequently, swelling of the joints was measured and the mucosa of the joints and the damage to bone and cartilage were examined at the fine-tissue level. Injection of a vimentin peptide inhibited swelling of the joints by 41% and inflammation of the mucosa of the joints by 38%, with the physiological saline solution having no influence. However, when a plurality of peptides of the mutated vimentin were combined, it was possible to virtually completely control said inflammation.

Regulatory T lymphocytes are regarded as promising mediators of peripheral tolerance. Therefore said animals were furthermore investigated with respect to the question, whether a limited allo immune response induces the formation of regulatory cells in an antigen-specific manner. Said mice were found to produce, after such a treatment, immune cells which successfully suppress the division of antigen-specific immune cells, said cells being intrahepatic T-cell populations having the phenotype $CD4^+$ $CD45RC^{neg}$ (FIG. 2).

Example 7

Blocking of the Formation of Autoantibody Complexes In Vitro

In order to block antibody binding to mutated vimentin, the following substances were used individually or in combination at a final concentration of 1 µg/ml:
1 Epicatechin (EC)
2 Epigallocatechin gallate (EGCG)
3 DMSO extract from green tea
4 Mutated vimentin 1.4 mg/ml
5 Mutated vimentin 0.7 mg/ml
6 Citrullinated vimentin 1.5 mg/ml To prepare an extract from green tea, 5 g of any commercially available tea were covered with 10 ml of 80% DMSO and stirred overnight. The solution was centrifuged at 13 000 rpm for 10. min and defined as tea extract. In contrast to the above solid substances 1, 2 and 4-6, 10 µl/ml tea extract of this preparation were employed. Antibody binding in the presence and absence of substances was analyzed in an ELISA for which microtiter plates were prepared analogously to Example 2. Different sera of RA patients were used in dilutions of from 1:100 to 1:400. Blocking of antibody binding was induced by preincubating 100 µl of the diluted serum with the substances or tea solutions indicated for 10 min. Subsequently, the remaining crossreaction was analyzed by transferring the 100 µl of serum-substance mixture to the cavities of said microtiter plate. According to the procedure of a classical ELISA, the bound antibodies were detected by means of a HRP-conjugated anti-human IgG. FIG. 3 depicts by way of example the results obtained using patient serum No. 400725.

FIG. 4 depicts the specificity of inhibition of autoantibodies from RA patients (antibodies to mutated vimentin) by extracts from green tea.

Example 8

Blocking of the Formation of Autoantibody Complexes In Vivo

Oral absorption of the catechins of green tea is very low with oral intake so that probably only minimal serum concentrations are achieved when enjoying tea in the normal way (Zhu et al., Oral absorption and bioavailability of tea catechins. Planta Medica 66 (2000) 444-7; see also Schrader et al., Bioverfügbarkeit verschiedener Tee-Catechine im Plasma in Abhängigkeit von der Darreichungsform [Bioavailability of various tea catechins in the plasma as a function of the dosage form]. Proc. Germ. Nutr. Soc. 3 (2001) 36).

Therefore the tea extracts prepared by us (see Example 7) were freeze-dried and reconstituted with cocoa oil or salmon oil. After oral administration of an extract prepared from 5 g of green tea (5 g/kg of body weight) to rats, blood was taken every half hour and analyzed by means of HPLC and GC/MS. About 2 hours after intake, a maximum plasma concentration of 75 µg/ml EC and EGCG (5-13% of the extract mass) and about 245 µg/ml for EGCG (content of 50% in the extract) in the rats was measured. Toxic effects did not occur in these animal experiments within the examination period of 1 month.

As a result of transferring these results to humans, this dosage form achieves plasma concentrations of tea ingredients (inter alia catechins), which could enable the formation of autoantibody complexes to be completely blocked.

Example 9

Efficacy of Extracts of Green Tea In Vitro

Figure 6:
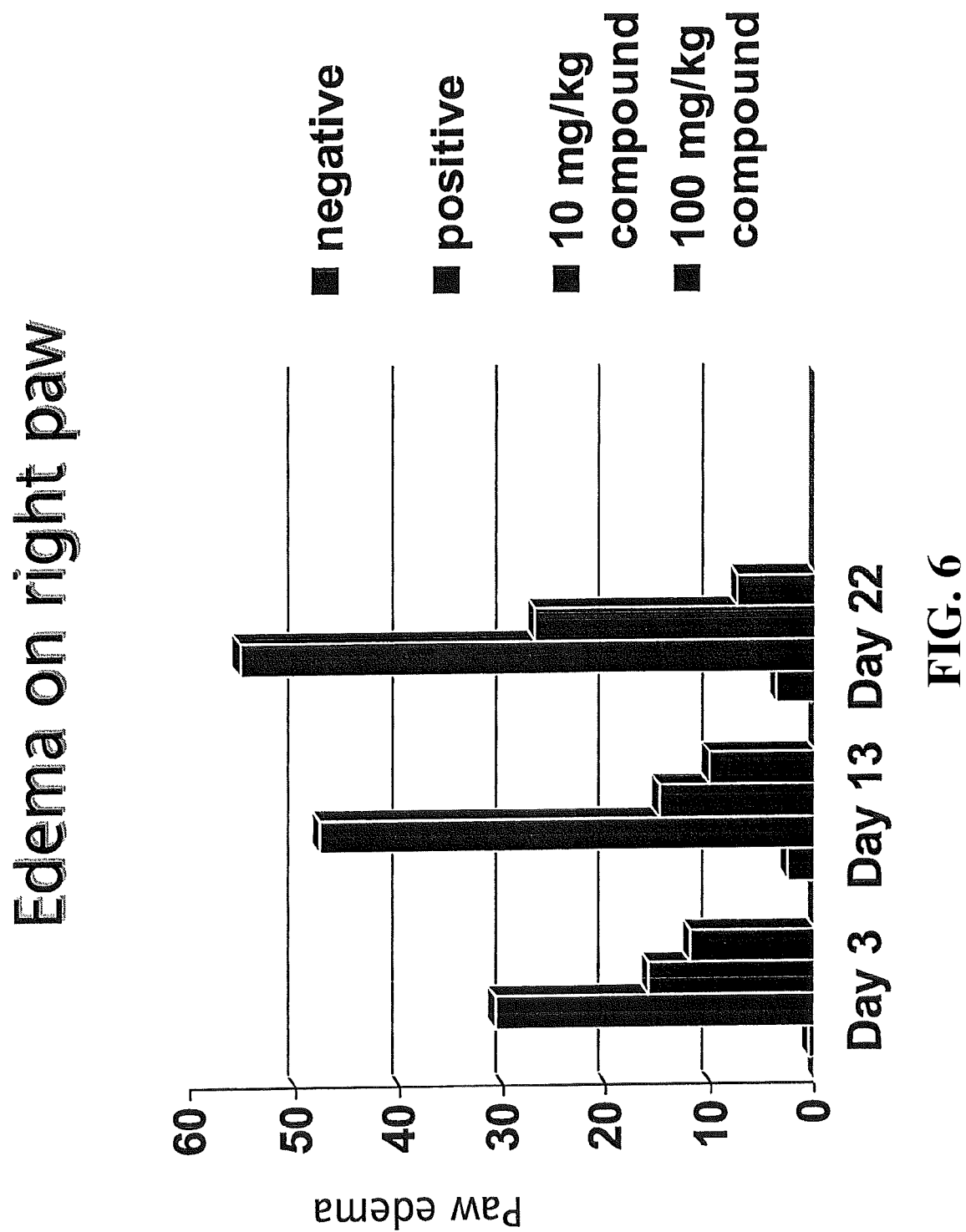
Figure 7:
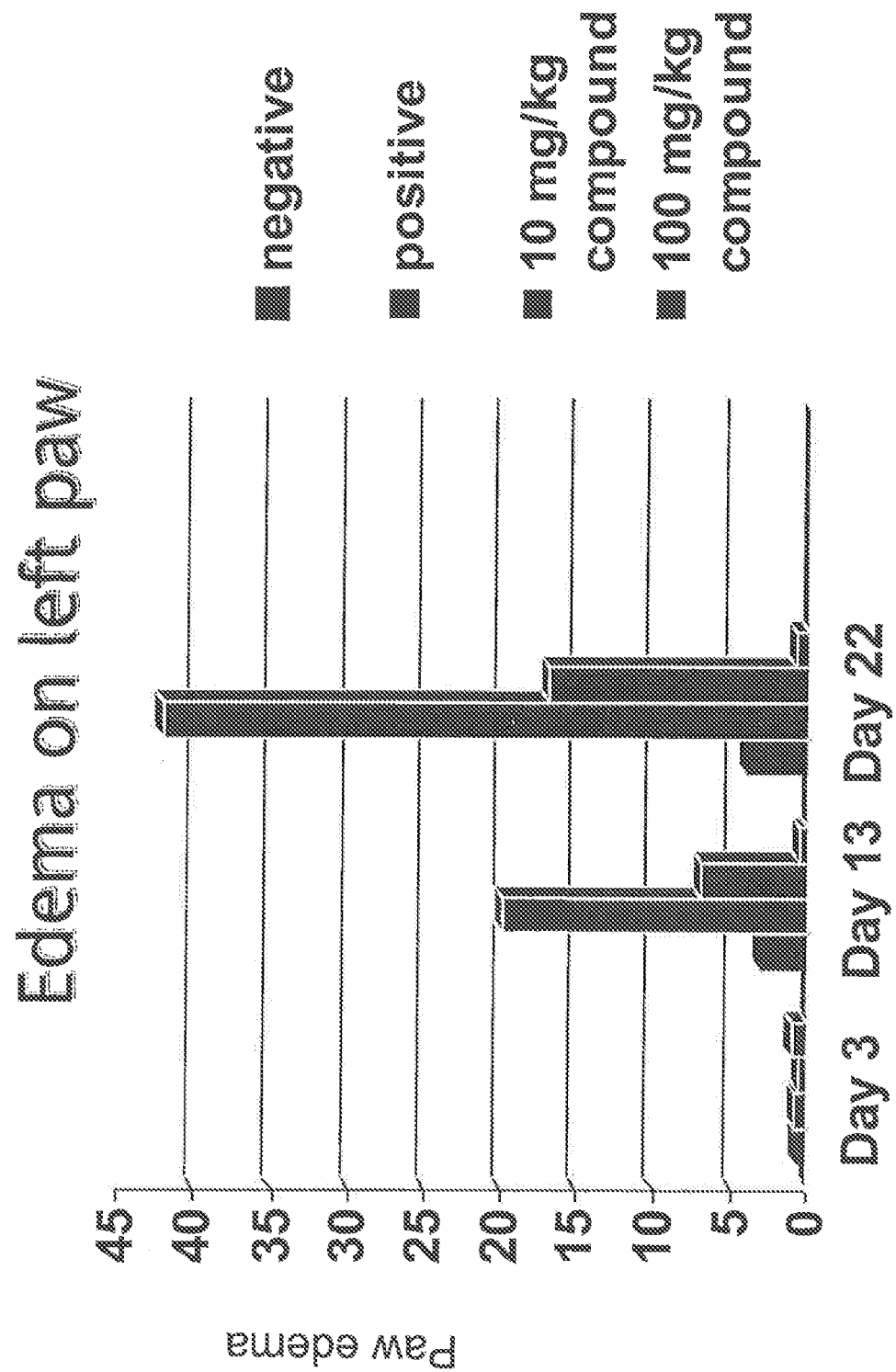
Figure 8:
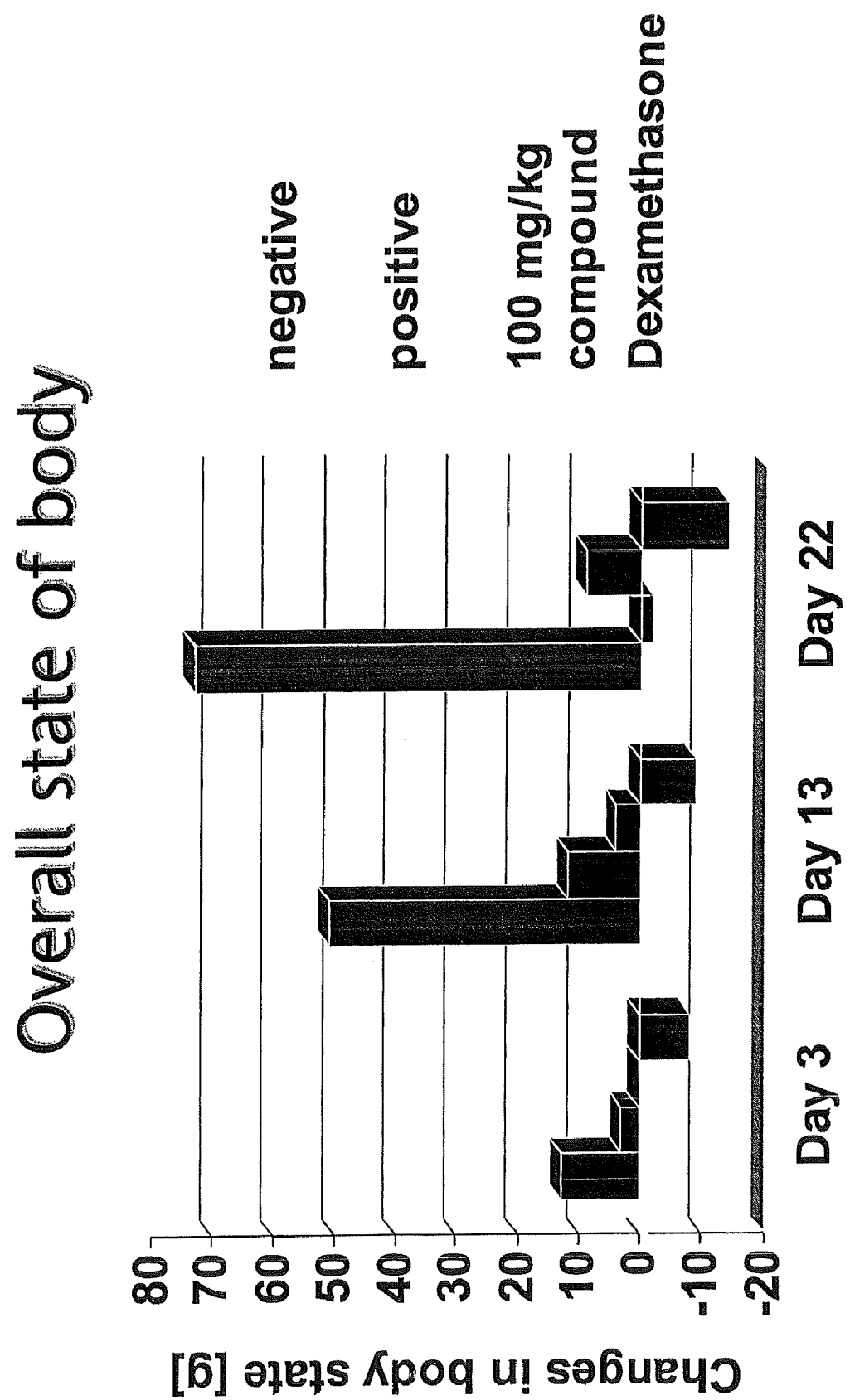

Intraperitoneal administration of an extract of green tea at concentrations of 10 and 100 mg, respectively, per kg of body weight exhibited a distinctly positive effect in an arthritis animal model (FIG. 5: determination of swelling of the paws after administration of adjuvant). FIGS. 6 to 8 depict the results.

We claim:

1. A polypeptide variant of native vimentin comprising SEQ ID NO: 1, wherein said polypeptide variant comprises an amino acid sequence wherein
at least one amino acid residue at position 16, 17, 19, 41, 58, 59, 60, 68, 76, 140, 142, 147, 363, 406 or 452 in said SEQ ID NO: 1 is substituted by arginine and wherein optionally
   (a) at least one amino acid residue at positions 3, 20, 33, 36, 37, 94, 165, 361, 399 or 426 in said SEQ ID NO: 1 is substituted by leucine;
   (b) at least one amino acid residue at positions 21, 41, 43, 50, 54, 62, 64 or 89 in said SEQ ID NO: 1 is substituted by proline;
   (c) at least one amino acid residue at positions 24, 35 or 99 in said SEQ ID NO: 1 is substituted by threonine; or
   (d) at least one amino acid residue at positions 25, 39, 42, 49, 55 or 67 in said SEQ ID NO: 1 is substituted by tyrosine.

2. The polypeptide variant according to claim 1, wherein at least two amino acid residues at said positions 16, 17, 19, 41, 58, 59, 60, 68, 76, 140, 142, 147, 363, 406 or 452 in said SEQ ID NO: 1 are substituted by arginine.

3. The polypeptide variant according to claim 2, wherein at least three amino acid residues at said positions 16, 17, 19, 41, 58, 59, 60, 68, 76, 140, 142, 147, 363, 406 or 452 in said SEQ ID NO: 1 are substituted by arginine.

4. The polypeptide variant according to claim 1, wherein at least one amino acid residue at positions 3, 20, 33, 36, 37, 94, 165, 361, 399 or 426 in said SEQ ID NO: 1 is substituted by leucine.

5. The polypeptide variant according to claim 4, wherein at least two amino acid residues at positions 3, 20, 33, 36, 37, 94, 165, 361, 399 or 426 in said SEQ ID NO: 1 is substituted by leucine.

6. The polypeptide variant according to claim 1, wherein at least one amino acid residue at positions 21, 41, 43, 50, 54, 62, 64 or 89 in said SEQ ID NO: 1 is substituted by proline.

7. The polypeptide variant according to claim 6, wherein at least two amino acid residue at said positions 21, 41, 43, 50, 54, 62, 64 or 89 in said SEQ ID NO: 1 are substituted by proline.

8. The polypeptide variant according to claim 1, wherein at least one amino acid residue at positions 24, 35 or 99 in said SEQ ID NO: 1 is substituted by threonine.

9. The polypeptide variant according to claim 8, wherein at least two amino acid residues at positions 24, 35 or 99 in said SEQ ID NO: 1 are substituted by threonine.

10. The polypeptide variant according to claim 1 wherein at least one amino acid residue at positions 25, 39, 42, 49, 55 or 67 in said SEQ ID NO: 1 is substituted by tyrosine.

11. The polypeptide variant according to claim 10, wherein at least two amino acid residues at said positions 25, 39, 42, 49, 55 or 67 in said SEQ ID NO: 1 are substituted by tyrosine.

12. The polypeptide variant according to claim 1, wherein at least one arginine residue in the variant polypeptide sequence is a citrulline residue.

13. The polypeptide variant according to claim 12, which has a citrulline residue in at least one of positions 4, 12, 23, 28, 36, 45, 50, 64, 71, 100, 320, 364 or 378 in the variant polypeptide sequence.

14. The polypeptide variant according to claim 13, which has a citrulline residue in at least two of said positions 4, 12, 23, 28, 36, 45, 50, 64, 71, 100, 320, 364 or 378 in the variant polypeptide sequence.

15. A polypeptide fragment which comprises at least six contiguous amino acids of a polypeptide variant of native vimentin and which exhibits reactivity to rheumatoid arthritis-associated autoantibodies, wherein said native vimentin comprises the amino acid sequence set forth in SEQ ID NO: 1 and said variant comprises an amino acid sequence which is located within the region of amino acids 30-70 of said SEQ ID NO: 1, wherein at least one amino acid residue at position 41, 58, 59, 60, or 68 in said SEQ ID NO: 1 is substituted for arginine, and wherein at least one of said six contiguous amino acids in said polypeptide fragment is said substituted arginine.

16. A peptide derivative which is a retro polypeptide, an inverso polypeptide or a cyclic polypeptide of a variant of native vimentin comprising SEQ ID NO: 1, wherein said variant comprises an amino acid sequence wherein at least one amino acid residue at position 16, 17, 19, 41, 58, 59, 60, 68, 76, 140, 142, 147, 363, 406 or 452 in said SEQ ID NO: 1 is substituted by arginine.

17. The polypeptide variant according to claim 1, which comprises the sequence set forth in SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9.

18. The polypeptide fragment according to claim 15, which comprises at least six contiguous amino acids of the polypeptide having amino acids 50-70 of said SEQ ID NO: 1, wherein at least one amino acid residue at position 58, 59, 60 or 68 in said SEQ ID NO: 1 is substituted by arginine.

19. The polypeptide fragment according to claim 15, which comprises amino acids 51-65 (C2) of said variant polypeptide sequence, wherein at least one amino acid residue in said fragment is said substituted arginine.

20. The polypeptide fragment according to claim 15, which comprises 17 amino acids of a variant vimentin polypeptide sequence set forth in SEQ ID NO: 9.

21. A polypeptide variant of native vimentin comprising SEQ ID NO: 1, wherein said variant comprises an amino acid sequence wherein glycine at positions 16, 41, 59 and 76 in said SEQ ID NO: 1 is substituted for arginine and which exhibits reactivity to rheumatoid arthritis-associated autoantibodies.

22. A 17-mer fragment of a polypeptide variant of native vimentin comprising SEQ ID NO: 1, wherein said polypeptide variant comprises an amino acid sequence wherein
(a) at least one glycine at amino acid residue at position 16, 17, 19, 41, 58, 59, 76, 140, 142, 147, 363, 406 or 452 in said SEQ ID NO: 1 is substituted by arginine; or
(b) at least one valine at amino acid residue at position 60 or 68 in said SEQ ID NO: 1 is substituted by arginine; or
(c) at least one glycine at amino acid residue at position 16, 17, 19, 41, 58, 59, 76, 140, 142, 147, 363, 406 or 452 in said SEQ ID NO: 1 is substituted by arginine and at least one valine at amino acid residue at position 60 or 68 in said SEQ ID NO: 1 is substituted by arginine;
wherein at least one of the 17 amino acids in said fragment of said polypeptide variant of native vimentin is said substituted arginine.

23. The fragment of claim 15 which is a 17-mer fragment, wherein at least one amino acid residue at position 41, 58, 59, 60, or 68 in said SEQ ID NO: 1 is substituted by arginine, and wherein at least one of said 17 amino acids in said polypeptide fragment is said substituted arginine.

24. The polypeptide variant according to claim 1, which comprises proline to threonine substitution in SEQ ID NO: 1, which variant comprises the polypeptide sequence of SEQ ID NO: 9.

25. The polypeptide variant according to claim 1, which comprises serine to tyrosine substitution in SEQ ID NO: 1, which variant comprises the polypeptide sequence of SEQ ID NO: 8.

26. The polypeptide variant according to claim 1, which comprises arginine to citrulline substitution in SEQ ID NO: 1, which variant comprises the polypeptide sequence of SEQ ID NO: 7.

27. A polypeptide fragment which comprises at least six contiguous amino acids of a polypeptide variant of native vimentin, which polypeptide variant comprises the amino acid sequence of SEQ ID NO: 9 and which further exhibits reactivity to rheumatoid arthritis-associated autoantibodies, wherein at least one of said six contiguous amino acids in said polypeptide fragment is the arginine at position 16, 17, 19, 41, 58, 59, 60, 68, 76, 140, 142, 147, 363, 406 or 452 in said SEQ ID NO: 9.

28. A diagnostic agent which comprises a polypeptide variant according to claim 1 and at least one customary component which is a buffer, a solvent, a carrier or a labeling group.

29. A diagnostic kit for detecting rheumatoid arthritis, which comprises, in one or separate packages, said diagnostic agent and said customary component according to claim 28.

30. The diagnostic kit as claimed in claim 29, wherein the carrier is DNA, RNA, a medically compatible polymer, a synthetic biopolymer or a protein.

31. A medicament, which comprises a polypeptide variant according to claim 1 and an acceptable carrier.

32. A medicament, which comprises the polypeptide fragment according to claim 15 and an acceptable carrier.

33. A process for in vitro detection of a rheumatoid arthritis, comprising contacting a body fluid of a subject with a diagnostic agent according to claim 28 or a kit comprising said diagnostic agent; and determining the concentration of autoantibodies in said body fluid of said subject, wherein said concentration is useful in the diagnosis, classification or evaluation of the severity of said rheumatic disease.

34. A method for the treatment of rheumatoid arthritis, comprising administering a polypeptide variant according to claim 1 to a subject in need thereof.

35. The method according to claim 34, further comprising administering epigallocatechin gallate (EGCG) to said subject.

36. The method according to claim 34, further comprising administering an extract of green tea to said subject.

37. The method according to claim 36, comprising administering an organic or organic-aqueous extract or a product obtainable from said green tea extract.

38. The method according to claim 36, wherein the active ingredient of said extract is epigallocatechin gallate (EGCG).

39. A method of making the polypeptide variant according to claim 1, comprising culturing a host cell which comprises a polynucleotide encoding said polypeptide variant under conditions sufficient to express said polypeptide; and harvesting said polypeptide.

\* \* \* \* \*

SEQUENCE LISTING

```
<160> NUMBER OF SEQ ID NOS: 9

<210> SEQ ID NO 1
<211> LENGTH: 466
<212> TYPE: PRT
<213> ORGANISM: Homo sapiens
<220> FEATURE:
<223> OTHER INFORMATION: Polypeptide sequence of native vimentin

<400> SEQUENCE: 1

Met Ser Thr Arg Ser Val Ser Ser Ser Tyr Arg Arg Met Phe Gly
 1               5                  10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
                35                  40                  45

Ser Arg Ser Leu Tyr Ala Ser Ser Pro Gly Gly Val Tyr Ala Thr Arg
            50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270
```

```
Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
        290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
        370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
        450                 455                 460

Leu Glu
465

<210> SEQ ID NO 2
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant I

<400> SEQUENCE: 2

Met Ser Thr Arg Ser Val Ser Ser Ser Tyr Arg Arg Met Phe Arg
1               5                   10                  15

Arg Pro Arg Thr Ala Ser Arg Pro Ser Ser Arg Ser Tyr Val Thr
                20                  25                  30

Thr Ser Thr Arg Thr Tyr Ser Leu Arg Ser Ala Leu Arg Pro Ser Thr
            35                  40                  45

Ser Arg Ser Leu Tyr Ala Ser Pro Arg Arg Val Tyr Ala Thr Arg
        50                  55                  60

Ser Ser Ala Val Arg Leu Arg Ser Ser Val Pro Arg Val Arg Leu Leu
65                  70                  75                  80

Gln Asp Ser Val Asp Phe Ser Leu Ala Asp Ala Ile Asn Thr Glu Phe
            85                  90                  95

Lys Asn Thr Arg Thr Asn Glu Lys Val Glu Leu Gln Glu Leu Asn Asp
        100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Arg Gln Arg Lys Ser
        130                 135                 140

Arg Leu Arg Asp Leu Tyr Glu Glu Glu Met Arg Glu Leu Arg Arg Gln
```

```
            145                 150                 155                 160
    Val Asp Gln Leu Thr Asn Asp Lys Ala Arg Val Glu Val Glu Arg Asp
                    165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
                195                 200                 205

Asp Val Asp Asn Ala Ser Leu Ala Arg Leu Asp Leu Glu Arg Lys Val
                210                 215                 220

Glu Ser Leu Gln Glu Glu Ile Ala Phe Leu Lys Lys Leu His Glu Glu
    225                 230                 235                 240

Glu Ile Gln Glu Leu Gln Ala Gln Ile Gln Glu Gln His Val Gln Ile
                    245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
                275                 280                 285

Glu Trp Tyr Lys Ser Lys Phe Ala Asp Leu Ser Glu Ala Ala Asn Arg
                290                 295                 300

Asn Asn Asp Ala Leu Arg Gln Ala Lys Gln Glu Ser Thr Glu Tyr Arg
    305                 310                 315                 320

Arg Gln Val Gln Ser Leu Thr Cys Glu Val Asp Ala Leu Lys Gly Thr
                    325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Arg Arg Leu Gln Asp Glu
                355                 360                 365

Ile Gln Asn Met Lys Glu Met Ala Arg His Leu Arg Glu Tyr Gln
                370                 375                 380

Asp Leu Leu Asn Val Lys Met Ala Leu Asp Ile Glu Ile Ala Thr Tyr
    385                 390                 395                 400

Arg Lys Leu Leu Glu Arg Glu Ser Arg Ile Ser Leu Pro Leu Pro
                    405                 410                 415

Asn Phe Ser Ser Leu Asn Leu Arg Glu Thr Asn Leu Asp Ser Leu Pro
                420                 425                 430

Leu Val Asp Thr His Ser Lys Arg Thr Leu Leu Ile Lys Thr Val Glu
                435                 440                 445

Thr Arg Asp Arg Gln Val Ile Asn Glu Thr Ser Gln His His Asp Asp
    450                 455                 460

Leu Glu
    465

<210> SEQ ID NO 3
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant II

<400> SEQUENCE: 3

Met Ser Leu Arg Ser Val Ser Ser Ser Tyr Arg Arg Met Phe Gly
1               5                   10                  15

Arg Pro Gly Leu Ala Ser Arg Pro Ser Ser Ser Arg Ser Tyr Val Thr
                20                  25                  30
```

```
Leu Ser Leu Arg Leu Tyr Ser Leu Arg Ser Ala Leu Arg Pro Ser Thr
         35                  40                  45

Ser Arg Ser Leu Tyr Ala Ser Ser Pro Arg Gly Asp Tyr Ala Ser Gln
 50                      55                  60

Asn Arg Trp Val Arg Leu Arg Ser Ser Val Pro Arg Val Arg Leu Leu
 65                  70                  75                  80

Gln Asp Ser Val Asp Phe Ser Leu Ala Asp Ala Ile Asn Leu Glu Phe
                 85                  90                  95

Lys Asn Thr Arg Thr Asn Glu Lys Val Glu Leu Gln Glu Leu Asn Asp
             100                 105                 110

Arg Phe Ala Asn Tyr Ile Asp Lys Val Arg Phe Leu Glu Gln Gln Asn
         115                 120                 125

Lys Ile Leu Leu Ala Glu Leu Glu Gln Leu Lys Gly Gln Arg Lys Ser
 130                 135                 140

Arg Leu Gly Asp Leu Tyr Glu Glu Glu Met Arg Glu Leu Arg Arg Gln
 145                 150                 155                 160

Val Asp Gln Leu Leu Asn Asp Lys Ala Arg Val Glu Val Glu Arg Asp
                 165                 170                 175

Asn Leu Ala Glu Asp Ile Met Arg Leu Arg Glu Lys Leu Gln Glu Glu
             180                 185                 190

Met Leu Gln Arg Glu Glu Ala Glu Asn Thr Leu Gln Ser Phe Arg Gln
         195                 200                 205

Asp Val Asp Asn Ala Ser Leu Ala Arg Leu Asp Leu Glu Arg Lys Val
 210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                 245                 250                 255

Asp Val Asp Val Ser Lys Pro Asp Leu Thr Ala Ala Leu Arg Asp Val
             260                 265                 270

Arg Gln Gln Tyr Glu Ser Val Ala Ala Lys Asn Leu Gln Glu Ala Glu
         275                 280                 285

Glu Trp Tyr Lys Ser Lys Phe Ala Asp Leu Ser Glu Ala Ala Asn Arg
 290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                 325                 330                 335

Asn Glu Ser Leu Glu Arg Gln Met Arg Glu Met Glu Glu Asn Phe Ala
             340                 345                 350

Val Glu Ala Ala Asn Tyr Gln Asp Leu Ile Gly Arg Leu Gln Asp Glu
         355                 360                 365

Ile Gln Asn Met Lys Glu Glu Met Ala Arg His Leu Arg Glu Tyr Gln
 370                 375                 380

Asp Leu Leu Asn Val Lys Met Ala Leu Asp Ile Glu Ile Ala Leu Tyr
385                 390                 395                 400

Arg Lys Leu Leu Glu Arg Glu Glu Ser Arg Ile Ser Leu Pro Leu Pro
                 405                 410                 415

Asn Phe Ser Ser Leu Asn Leu Arg Glu Leu Asn Leu Asp Ser Leu Pro
             420                 425                 430

Leu Val Asp Thr His Ser Lys Arg Thr Leu Leu Ile Lys Thr Val Glu
         435                 440                 445

Thr Arg Asp Arg Gln Val Ile Asn Glu Thr Ser Gln His His Asp Asp
```

```
                   450                 455                 460
Leu Glu
465

<210> SEQ ID NO 4
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant III

<400> SEQUENCE: 4

Met Ser Thr Arg Ser Val Ser Ser Ser Tyr Arg Gly Met Phe Gly
1               5                   10                  15

Arg Pro Gly Thr Ala Ser Gly Pro Ser Ser Arg Ser Tyr Val Thr
                20                  25                  30

Thr Ser Thr Arg Thr Tyr Ser Leu Arg Ser Ala Leu Gly Pro Ser Thr
                35                  40                  45

Ser Arg Ser Leu Tyr Ala Ser Ser Pro Gly Arg Val Tyr Ala Thr Gly
        50                  55                  60

Ser Ser Tyr Val Arg Leu Arg Ser Val Pro Arg Val Gly Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
        130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
                195                 200                 205

Asp Val Asp Asn Ala Ser Leu Ala Arg Leu Asp Leu Glu Arg Lys Val
        210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
                275                 280                 285

Glu Trp Tyr Lys Ser Lys Phe Ala Asp Leu Ser Glu Ala Ala Asn Arg
        290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335
```

```
Asn Glu Ser Leu Glu Arg Gln Met Arg Glu Met Glu Asn Phe Ala
            340                 345                 350
Val Glu Ala Ala Asn Tyr Gln Asp Thr Ile Gly Gly Leu Gln Asp Glu
            355                 360                 365
Ile Gln Asn Met Lys Glu Met Ala Gly His Leu Arg Glu Tyr Gln
        370                 375                 380
Asp Leu Leu Asn Val Lys Met Ala Leu Asp Ile Glu Ile Ala Thr Tyr
385                 390                 395                 400
Gly Lys Leu Leu Glu Gly Glu Ser Arg Ile Ser Leu Pro Leu Pro
                405                 410                 415
Asn Phe Ser Ser Leu Asn Leu Gly Glu Thr Asn Leu Asp Ser Leu Pro
                420                 425                 430
Leu Val Asp Thr His Ser Lys Arg Thr Leu Leu Ile Lys Thr Val Glu
                435                 440                 445
Thr Arg Asp Arg Gln Val Ile Asn Glu Thr Ser Gln His His Asp Asp
        450                 455                 460
Leu Glu
465

<210> SEQ ID NO 5
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant IV

<400> SEQUENCE: 5

Met Ser Thr Arg Ser Val Ser Ser Ser Tyr Arg Gly Met Phe Gly
1               5                   10                  15
Arg Pro Gly Thr Ala Ser Arg Pro Ser Ser Arg Ser Tyr Val Thr
            20                  25                  30
Thr Ser Thr Arg Thr Tyr Ser Leu Pro Ser Ala Leu Gly Pro Ser Thr
        35                  40                  45
Ser Pro Ser Leu Tyr Ala Ser Pro Gly Gly Arg Tyr Ala Thr Pro
50                  55                  60
Ser Ser Tyr Arg Gly Leu Arg Ser Ser Val Pro Arg Val Gly Leu Leu
65                  70                  75                  80
Gln Asp Ser Val Asp Phe Ser Leu Ala Asp Ala Ile Asn Thr Glu Phe
                85                  90                  95
Lys Asn Thr Arg Thr Asn Glu Lys Val Glu Leu Gln Glu Leu Asn Asp
            100                 105                 110
Arg Phe Ala Asn Tyr Ile Asp Lys Val Arg Phe Leu Glu Gln Gln Asn
        115                 120                 125
Lys Ile Leu Leu Ala Glu Leu Glu Gln Leu Lys Gly Gln Gly Lys Ser
    130                 135                 140
Arg Leu Gly Asp Leu Tyr Glu Glu Glu Met Arg Glu Leu Arg Arg Gln
145                 150                 155                 160
Val Asp Gln Leu Thr Asn Asp Lys Ala Arg Val Glu Val Glu Arg Asp
                165                 170                 175
Asn Leu Ala Glu Asp Ile Met Arg Leu Arg Glu Lys Leu Gln Glu Glu
            180                 185                 190
Met Leu Gln Arg Glu Glu Ala Glu Asn Thr Leu Gln Ser Phe Arg Gln
        195                 200                 205
Asp Val Asp Asn Ala Ser Leu Ala Arg Leu Asp Leu Glu Arg Lys Val
    210                 215                 220
```

```
Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
            245                 250                 255

Asp Val Asp Val Ser Lys Pro Asp Leu Thr Ala Ala Leu Arg Asp Val
        260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
        290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
            325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
            405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
        450                 455                 460

Leu Glu
465
```

```
<210> SEQ ID NO 6
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant V
<220> FEATURE:
<221> NAME/KEY: MOD_RES
<222> LOCATION: (64)..(64)
<223> OTHER INFORMATION: Citrulline

<400> SEQUENCE: 6

Met Ser Thr Arg Ser Val Ser Ser Ser Tyr Arg Arg Met Phe Arg
1               5                   10                  15

Arg Pro Arg Thr Pro Ser Arg Pro Ser Ser Arg Ser Tyr Val Thr
                20                  25                  30

Thr Ser Thr Arg Thr Tyr Ser Leu Arg Ser Pro Leu Arg Pro Ser Thr
            35                  40                  45

Ser Arg Ser Leu Tyr Pro Ser Ser Pro Thr Arg Tyr Pro Thr Xaa
        50                  55                  60

Ser Ser Ala Val Arg Leu Arg Ser Ser Val Pro Arg Val Arg Leu Leu
65                  70                  75                  80
```

```
Gln Asp Ser Val Asp Phe Ser Leu Pro Asp Ala Ile Asn Thr Glu Phe
             85                  90                  95
Lys Asn Thr Arg Thr Asn Glu Lys Val Glu Leu Gln Glu Leu Asn Asp
            100                 105                 110
Arg Phe Ala Asn Tyr Ile Asp Lys Val Arg Phe Leu Glu Gln Gln Asn
        115                 120                 125
Lys Ile Leu Leu Ala Glu Leu Glu Gln Leu Lys Arg Gln Arg Lys Ser
130                 135                 140
Arg Leu Arg Asp Leu Tyr Glu Glu Glu Met Arg Glu Leu Arg Arg Gln
145                 150                 155                 160
Val Asp Gln Leu Thr Asn Asp Lys Ala Arg Val Glu Val Glu Arg Asp
                165                 170                 175
Asn Leu Ala Glu Asp Ile Met Arg Leu Arg Glu Lys Leu Gln Glu Glu
            180                 185                 190
Met Leu Gln Arg Glu Glu Ala Glu Asn Thr Leu Gln Ser Phe Arg Gln
        195                 200                 205
Asp Val Asp Asn Ala Ser Leu Ala Arg Leu Asp Leu Glu Arg Lys Val
210                 215                 220
Glu Ser Leu Gln Glu Glu Ile Ala Phe Leu Lys Lys Leu His Glu Glu
225                 230                 235                 240
Glu Ile Gln Glu Leu Gln Ala Gln Ile Gln Glu Gln His Val Gln Ile
                245                 250                 255
Asp Val Asp Val Ser Lys Pro Asp Leu Thr Ala Ala Leu Arg Asp Val
            260                 265                 270
Arg Gln Gln Tyr Glu Ser Val Ala Ala Lys Asn Leu Gln Glu Ala Glu
        275                 280                 285
Glu Trp Tyr Lys Ser Lys Phe Ala Asp Leu Ser Glu Ala Ala Asn Arg
290                 295                 300
Asn Asn Asp Ala Leu Arg Gln Ala Lys Gln Glu Ser Thr Glu Tyr Arg
305                 310                 315                 320
Arg Gln Val Gln Ser Leu Thr Cys Glu Val Asp Ala Leu Lys Gly Thr
                325                 330                 335
Asn Glu Ser Leu Glu Arg Gln Met Arg Glu Met Glu Glu Asn Phe Ala
            340                 345                 350
Val Glu Ala Ala Asn Tyr Gln Asp Thr Ile Gly Arg Leu Gln Asp Glu
        355                 360                 365
Ile Gln Asn Met Lys Glu Glu Met Ala Arg His Leu Arg Glu Tyr Gln
370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ser Leu Pro Leu Pro
                405                 410                 415
Asn Phe Ser Ser Leu Asn Leu Arg Glu Thr Asn Leu Asp Ser Leu Pro
            420                 425                 430
Leu Val Asp Thr His Ser Lys Arg Thr Leu Leu Ile Lys Thr Val Glu
        435                 440                 445
Thr Arg Asp Gly Gln Val Ile Asn Glu Thr Ser Gln His His Asp Asp
450                 455                 460
Leu Glu
465

<210> SEQ ID NO 7
<211> LENGTH: 466
<212> TYPE: PRT
```

<213> ORGANISM: Artificial Sequence
<220> FEATURE:
<223> OTHER INFORMATION: Description of Artificial Sequence: Synthetic
      polypeptide sequence of mutant VI
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (12)..(12)
<223> OTHER INFORMATION: Citrulline
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (36)..(36)
<223> OTHER INFORMATION: Citrulline
<220> FEATURE:
<221> NAME/KEY: MOD_RES
<222> LOCATION: (45)..(45)
<223> OTHER INFORMATION: Citrulline
<220> FEATURE:
<221> NAME/KEY: MOD_RES
<222> LOCATION: (64)..(64)
<223> OTHER INFORMATION: Citrulline
<220> FEATURE:
<221> NAME/KEY: MOD_RES
<222> LOCATION: (71)..(71)
<223> OTHER INFORMATION: Citrulline
<220> FEATURE:
<221> NAME/KEY: MOD_RES
<222> LOCATION: (320)..(320)
<223> OTHER INFORMATION: Citrulline
<220> FEATURE:
<221> NAME/KEY: MOD_RES
<222> LOCATION: (364)..(364)
<223> OTHER INFORMATION: Citrulline
<220> FEATURE:
<221> NAME/KEY: MOD_RES
<222> LOCATION: (378)..(378)
<223> OTHER INFORMATION: Citrulline

<400> SEQUENCE: 7

Met Ser Thr Xaa Ser Val Ser Ser Ser Tyr Xaa Arg Met Phe Gly
1               5                   10                  15

Gly Pro Gly Thr Ala Ser Xaa Pro Ser Ser Arg Ser Tyr Val Thr
                20                  25                  30

Thr Ser Thr Xaa Thr Tyr Ser Leu Gly Ser Ala Leu Xaa Pro Ser Thr
                35                  40                  45

Ser Arg Ser Leu Tyr Ala Ser Ser Pro Gly Arg Val Tyr Ala Thr Xaa
        50                  55                  60

Ser Ser Tyr Val Arg Leu Xaa Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
            130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

```
Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
    260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Xaa
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Xaa Leu Gln Asp Glu
        355                 360                 365

Ile Gln Asn Met Lys Glu Glu Met Ala Xaa His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465

<210> SEQ ID NO 8
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant VII
<220> FEATURE:
<221> NAME/KEY: MOD_RES
<222> LOCATION: (23)..(23)
<223> OTHER INFORMATION: Citrulline
<220> FEATURE:
<221> NAME/KEY: MOD_RES
<222> LOCATION: (28)..(28)
<223> OTHER INFORMATION: Citrulline
<220> FEATURE:
<221> NAME/KEY: MOD_RES
<222> LOCATION: (36)..(36)
<223> OTHER INFORMATION: Citrulline
<220> FEATURE:
```

<220> FEATURE:
<221> NAME/KEY: MOD_RES
<222> LOCATION: (45)..(45)
<223> OTHER INFORMATION: Citrulline
<220> FEATURE:
<221> NAME/KEY: MOD_RES
<222> LOCATION: (50)..(50)
<223> OTHER INFORMATION: Citrulline
<220> FEATURE:
<221> NAME/KEY: MOD_RES
<222> LOCATION: (64)..(64)
<223> OTHER INFORMATION: Citrulline
<220> FEATURE:
<221> NAME/KEY: MOD_RES
<222> LOCATION: (71)..(71)
<223> OTHER INFORMATION: Citrulline
<220> FEATURE:
<221> NAME/KEY: MOD_RES
<222> LOCATION: (100)..(100)
<223> OTHER INFORMATION: Citrulline
<220> FEATURE:
<221> NAME/KEY: MOD_RES
<222> LOCATION: (450)..(450)
<223> OTHER INFORMATION: Citrulline

<400> SEQUENCE: 8

```
Met Ser Thr Arg Ser Val Ser Ser Ser Tyr Arg Arg Met Phe Gly
1               5                   10                  15

Gly Pro Gly Thr Ala Ser Xaa Thr Tyr Ser Ser Xaa Gly Tyr Val Thr
            20                  25                  30

Leu Ser Thr Xaa Thr Tyr Tyr Leu Gly Tyr Ala Leu Xaa Pro Ser Thr
            35                  40                  45

Tyr Xaa Ser Leu Tyr Ala Tyr Ser Pro Gly Gly Val Tyr Ala Thr Xaa
    50                  55                  60

Gly Ser Tyr Arg Arg Leu Xaa Gly Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Xaa Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285
```

```
Glu Trp Tyr Lys Ser Lys Phe Ala Asp Leu Ser Ala Ala Asn Arg
    290                 295                 300
Asn Asn Asp Ala Leu Arg Gln Ala Lys Gln Glu Ser Thr Glu Tyr Arg
305                 310                 315                 320
Arg Gln Val Gln Ser Leu Thr Cys Glu Val Asp Ala Leu Lys Gly Thr
                325                 330                 335
Asn Glu Ser Leu Glu Arg Gln Met Arg Glu Met Glu Glu Asn Phe Ala
                340                 345                 350
Val Glu Ala Ala Asn Tyr Gln Asp Thr Ile Gly Arg Leu Gln Asp Glu
                355                 360                 365
Ile Gln Asn Met Lys Glu Met Ala Arg His Leu Arg Glu Tyr Gln
    370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ser Leu Pro Leu Pro
                405                 410                 415
Asn Phe Ser Ser Leu Asn Leu Arg Glu Thr Asn Leu Asp Ser Leu Pro
                420                 425                 430
Leu Val Asp Thr His Ser Lys Arg Thr Leu Leu Ile Lys Thr Val Glu
                435                 440                 445
Thr Xaa Asp Gly Gln Val Ile Asn Glu Thr Ser Gln His His Asp Asp
    450                 455                 460
Leu Glu
465

<210> SEQ ID NO 9
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide sequence of mutant VIII

<400> SEQUENCE: 9

Met Ser Thr Arg Ser Val Ser Ser Ser Tyr Arg Arg Met Phe Arg
1               5                   10                  15
Gly Thr Gly Thr Ala Ser Arg Thr Ser Ser Ser Arg Ser Tyr Val Thr
                20                  25                  30
Thr Ser Thr Arg Thr Tyr Ser Leu Arg Ser Ala Leu Arg Thr Ser Thr
                35                  40                  45
Ser Arg Ser Leu Tyr Tyr Ser Pro Gly Arg Val Tyr Ala Thr Arg
    50                  55                  60
Ser Ser Tyr Val Arg Leu Arg Ser Ser Val Thr Arg Val Ser Leu Leu
65                  70                  75                  80
Gln Asp Ser Val Asp Phe Ser Leu Ala Asp Ala Ile Asn Thr Glu Phe
                85                  90                  95
Lys Asn Thr Arg Thr Asn Glu Lys Val Glu Leu Gln Glu Leu Asn Asp
                100                 105                 110
Arg Phe Ala Asn Tyr Ile Asp Lys Val Arg Phe Leu Glu Gln Gln Asn
                115                 120                 125
Lys Ile Leu Leu Ala Glu Leu Glu Gln Leu Lys Gly Gln Gly Lys Ser
                130                 135                 140
Arg Leu Gly Asp Leu Tyr Glu Glu Glu Met Arg Glu Leu Arg Arg Gln
145                 150                 155                 160
Val Asp Gln Leu Thr Asn Asp Lys Ala Arg Val Glu Val Glu Arg Asp
```

-continued

```
                165                 170                 175
Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
            245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
            290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
    450                 455                 460

Leu Glu
465
```